US007759651B2

(12) United States Patent
Knight et al.

(10) Patent No.: US 7,759,651 B2
(45) Date of Patent: Jul. 20, 2010

(54) OPTICAL RADIATION SENSOR SYSTEM AND METHOD FOR MEASURING RADIATION TRANSMITTANCE OF A FLUID

(75) Inventors: Douglas Gordon Knight, London (CA); Alex M. W. Verdun, London (CA); Peter Van-Doodewaard, Taylors, SC (US)

(73) Assignee: Trojan Technologies, London (CA)

( * ) Notice: Subject to any disclaimer, the term of this patent is extended or adjusted under 35 U.S.C. 154(b) by 91 days.

(21) Appl. No.: 11/578,832

(22) PCT Filed: Apr. 19, 2005

(86) PCT No.: PCT/CA2005/000595

§ 371 (c)(1),
(2), (4) Date: Jul. 31, 2007

(87) PCT Pub. No.: WO2005/100956

PCT Pub. Date: Oct. 27, 2005

(65) Prior Publication Data

US 2008/0087836 A1    Apr. 17, 2008

Related U.S. Application Data

(60) Provisional application No. 60/562,974, filed on Apr. 19, 2004.

(51) Int. Cl.
*G01N 21/17* (2006.01)
(52) U.S. Cl. ........................ 250/373; 250/372
(58) Field of Classification Search ............... 250/372, 250/373
See application file for complete search history.

(56) References Cited

U.S. PATENT DOCUMENTS

| 3,655,979 | A | * | 4/1972 | Jernigan, Jr. | 378/55 |
| 4,290,695 | A |   | 9/1981 | Schmitt |  |
| 4,358,960 | A | * | 11/1982 | Porter | 73/705 |

(Continued)

FOREIGN PATENT DOCUMENTS

CA    2411975    12/2001

(Continued)

OTHER PUBLICATIONS

International Search Report issued in PCT/CA2005/000595 dated Jul. 25, 2005.

*Primary Examiner*—David P Porta
*Assistant Examiner*—Mark R Gaworecki
(74) *Attorney, Agent, or Firm*—Katten Muchin Rosenman LLP

(57) ABSTRACT

A process for measuring transmittance of a fluid with first and second radiation wavelengths includes (i) positioning a polychromatic radiation source and a polychromatic radiation sensor in a spaced relationship to define a first thickness of fluid; (ii) detecting a first radiation intensity corresponding to the first wavelength at the first thickness; (iii) detecting a second radiation intensity corresponding to the second wavelength at the first thickness; (iv) altering the first thickness to define a second thickness; (v) detecting a third radiation intensity corresponding to the first wavelength at the second thickness; (vi) detecting a fourth radiation intensity corresponding to the second wavelength at the second thickness; and (vii) calculating radiation transmittance of the fluid in the radiation field from the first radiation intensity, the second radiation intensity, the third radiation intensity and the fourth radiation intensity.

34 Claims, 3 Drawing Sheets

U.S. PATENT DOCUMENTS

Figure 1:
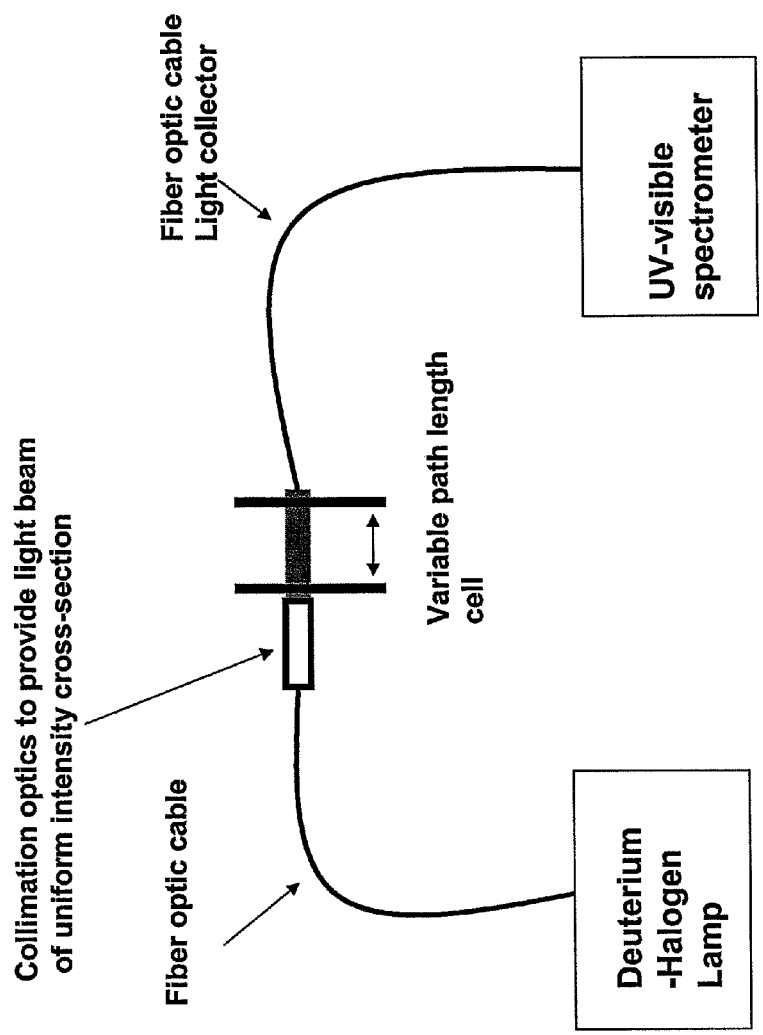
Figure 2:
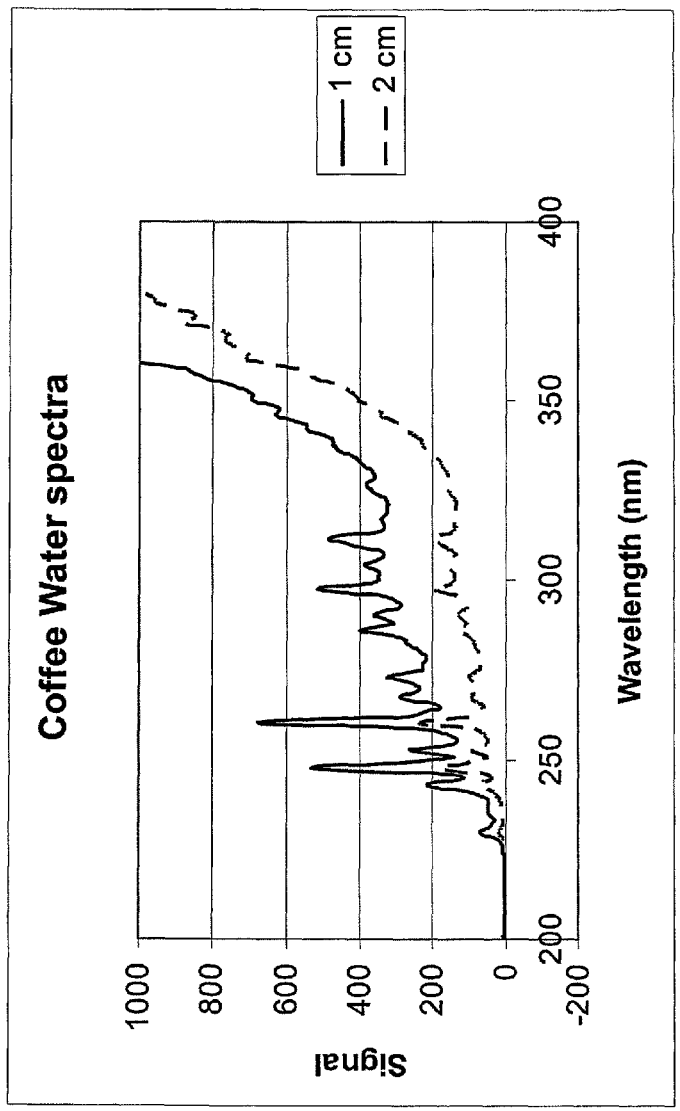
Figure 3:
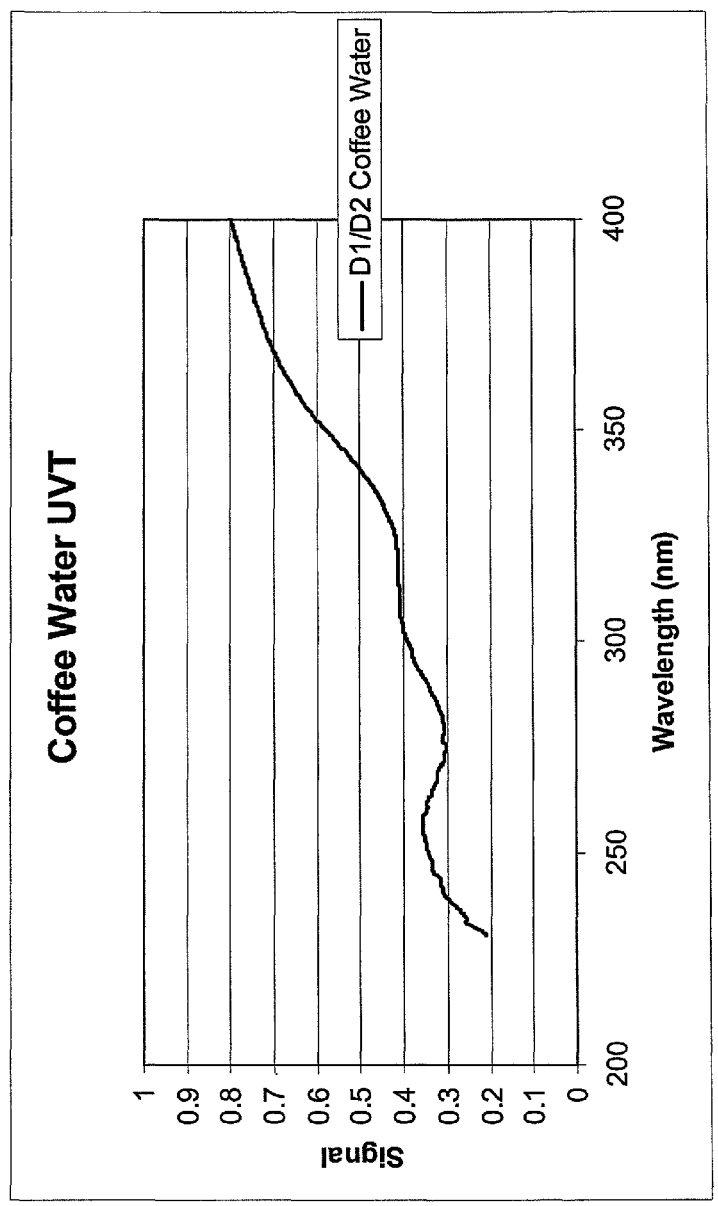

| | | |
|---|---|---|
| 4,482,809 A | 11/1984 | Maarschalkerweerd |
| 4,602,162 A | 7/1986 | Sperry, III et al. |
| 4,872,980 A | 10/1989 | Maarschalkerweerd |
| 5,006,244 A | 4/1991 | Maarschalkerweerd |
| 5,194,921 A * | 3/1993 | Tambo et al. ............... 356/432 |
| 5,242,602 A * | 9/1993 | Richardson et al. ......... 210/745 |
| 5,371,020 A | 12/1994 | Frischauf |
| 5,418,370 A | 5/1995 | Maarschalkerweerd |
| 5,504,335 A | 4/1996 | Maarschalkerweerd |
| 5,539,210 A | 7/1996 | Maarschalkerweerd |
| 6,057,917 A * | 5/2000 | Petersen et al. ............. 356/213 |
| RE36,896 E | 10/2000 | Maarschalkerweerd |
| 2002/0036274 A1 | 3/2002 | Ellis et al. |
| 2003/0153844 A1 * | 8/2003 | Smith et al. ................. 600/573 |

FOREIGN PATENT DOCUMENTS

| | | |
|---|---|---|
| JP | 10057954 | 3/1998 |
| NL | 1003961 | 3/1998 |
| WO | WO 01/96823 | 12/2001 |

* cited by examiner

OPTICAL RADIATION SENSOR SYSTEM AND METHOD FOR MEASURING RADIATION TRANSMITTANCE OF A FLUID

CROSS-REFERENCE TO RELATED APPLICATIONS

This application is a National Stage Entry of International Application No. PCT/CA2005/000595 filed Apr. 19, 2005, which claims priority to U.S. Provisional Application No. 60/562,974 filed Apr. 19, 2004.

BACKGROUND OF THE INVENTION

1. Field of the Invention

In one of its aspects, the present invention relates to an optical radiation sensor system. In another of its aspects, the present invention relates to a method for measuring radiation transmittance of a fluid.

2. Description of the Prior Art

Optical radiation sensors are known and find widespread use in a number of applications. One of the principal applications of optical radiation sensors is in the field of ultraviolet radiation fluid disinfection systems.

It is known that the irradiation of water with ultraviolet light will disinfect the water by inactivation of microorganisms in the water, provided the irradiance and exposure duration are above a minimum "dose" level (often measured in units of milliWatt seconds per square centimetre or $mW*s/cm^2$). Ultraviolet water disinfection units such as those commercially available from Trojan Technologies Inc. under the tradenames Trojan UVMax™, Trojan UVSwift™ and Trojan UVLogic™, employ this principle to disinfect water for human consumption. Generally, water to be disinfected passes through a pressurized stainless steel cylinder which is flooded with ultraviolet radiation. Large scale municipal waste water treatment equipment such as that commercially available from Trojan Technologies Inc. under the tradenames UV3000 and UV4000, employ the same principle to disinfect waste water. Generally, the practical applications of these treatment systems relates to submersion of a treatment module or system in an open channel wherein the wastewater is exposed to radiation as it flows past the lamps. For further discussion of fluid disinfection systems employing ultraviolet radiation, see any one of the following:

a. U.S. Pat. No. 4,482,809,
b. U.S. Pat. No. 4,872,980,
c. U.S. Pat. No. 5,006,244,
d. U.S. Pat. No. 5,418,370,
e. U.S. Pat. No. 5,504,335
f. U.S. Pat. No. 5,539,210, and
g. U.S. Pat. Re36,896.

In many applications, it is desirable to monitor the level of ultraviolet radiation present within the water (or other fluid) under treatment or other investigation. In this way, it is possible to assess, on a continuous or semi-continuous basis, the level of ultraviolet radiation, and thus the overall effectiveness and efficiency of the disinfection process.

It is known in the art to monitor the ultraviolet radiation level by deploying one or more passive sensor devices near the operating lamps in specific locations and orientations which are remote from the operating lamps. These passive sensor devices may be photodiodes, photoresistors or other devices that respond to the impingement of the particular radiation wavelength or range of radiation wavelengths of interest by producing a repeatable signal level (e.g., in volts or amperes) on output leads.

In most commercial ultraviolet water disinfection systems, the single largest operating cost relates to the cost of electricity to power the ultraviolet radiation lamps. In a case where the transmittance of the fluid varies from time to time, it would be very desirable to have a convenient means by which fluid transmittance could be measured for the fluid being treated by the system (or the fluid being otherwise investigated) at a given time. If it is found that fluid transmittance is relatively high, it might be possible to reduce power consumption in the lamps by reducing the output thereof. In this way, the significant savings in power costs would be possible.

The measurement of fluid transmittance is desirable since measurement of intensity alone is not sufficient to characterize the entire radiation field—i.e., it is not possible to separate the linear effects of lamp aging and fouling from exponential effects of transmittance. Further, dose delivery is a function of the entire radiation field, since not all fluid takes the same path.

The prior art has endeavoured to develop reliable radiation (particularly UV) transmittance measuring devices.

For example, it is known to use a single measurement approach. Unfortunately, the single measurement distance requires re-calibration with fluid of known transmittance to account for fouling.

It is also known to use a two-sensor system in which a first sensor is disposed in air and a second sensor is disposed in water. The problem with this approach is that it results in different fouling of each sensor with resulting errors.

Further, some systems require obtaining a sample from a channel of flowing fluid and thereafter measuring the radiation transmittance of the sample. Unfortunately, this approach necessitates the use of additional fluid handling measures which can lead to non-representative samples.

International Publication Number WO 01/96823 and published United States patent application 2002/0036274 [both in the name of Ellis et al. (Ellis) and assigned to the assignee of the present invention] teach an optical radiation sensor device for detecting radiation in a radiation field. A preferred embodiment of the device includes a radiation source and a radiation sensor element positioned to receive radiation from the radiation source. A motor (or other motive means) is provided to alter the thickness of the radiation field from a first thickness to a second thickness. The sensor element is capable of detecting and responding to incident radiation from a radiation source at the first thickness and at the second thickness. The optical radiation sensor device allows for determination of radiation (preferably ultraviolet radiation) transmittance of a fluid of interest.

Conventionally, radiation (e.g., ultraviolet radiation) transmittance of a fluid has been done by utilizing a monochromatic radiation—i.e., a radiation source that will emit a single wavelength of interest, so that the sensor element is used in a manner whereby a single wavelength of interest is detected and processed.

A problem with this conventional approach is that there can be significant errors in radiation transmittance calculated using the monochromatic measurement technique on a given fluid flow due to variation in radiation transmittance with the wavelength of the light that is detected and processed.

Thus, despite the advances made in the art, there exists a need for an improved device which can measure radiation transmittance of a fluid. Ideally, the device would be to respond to polychromatic radiation and measure UV transmittance of a fluid in an on-line or random measurement manner.

DISCLOSURE OF THE INVENTION

It is an object of the present invention to provide a novel fluid treatment system which obviates or mitigates at least one of the above-mentioned disadvantages of the prior art.

Accordingly, in one of its aspects, the present invention provides a process for measuring transmittance of a fluid in a radiation field comprising radiation at a first wavelength and radiation at a second wavelength different from the first wavelength, the process comprising the steps of:

(i) positioning a polychromatic radiation source and a polychromatic radiation sensor element in a spaced relationship to define a first thickness of fluid in the radiation field;

(ii) detecting a first radiation intensity corresponding to radiation at the first wavelength received by the sensor element at the first thickness;

(iii) detecting a second radiation intensity corresponding to radiation at the second wavelength received by the sensor element at the first thickness;

(iv) altering the first thickness to define a second thickness;

(v) detecting a third radiation intensity corresponding to radiation at the first wavelength received by the sensor element at the second thickness;

(vi) detecting a fourth radiation intensity corresponding to radiation at the second wavelength received by the sensor element at the second thickness; and (vii) calculating radiation transmittance of the fluid in the radiation field from the first radiation intensity, the second radiation intensity, the third radiation intensity and the fourth radiation intensity.

Thus, in a preferred embodiment, the present process relates to a novel manner to measure UV transmittance of a fluid in an on-line or random measurement manner. This preferred embodiment employs the use of a polychromatic radiation source (more preferably a medium pressure mercury lamp) and a polychromatic radiation sensor element (more preferably a filtered radiation sensor element).

Preferably, the process is carried out on a device such as taught by Ellis referred to above. The resulting sensor signal would be the sum of multiple (i.e., two or more) lamp lines within the detection limits.

The preferred polychromatic radiation source is an ultraviolet radiation source such as a medium pressure UV lamp, more particularly a miniature medium pressure UV lamp. Light sources other than miniature medium pressure UV lamps may also be used. For example it is possible utilize an ultraviolet semiconductor light emitting diode (LED) as the radiation source. This alternate radiation source is capable of emitting ~1 mW in the ~280 nm wavelength region.

To determine the optimum response curve for a filtered sensor in a polychromatic UVT system, the expression for the equivalent 254 nm dose from the EPA Ultraviolet Guidance Manual may be used. The equivalent 254 nm dose from polychromatic radiation is described as the weighted sum of the dosage from all wavelengths in the disinfection range, where the weighting is determined by the action spectrum of the target microbe. This dosage sum is therefore equivalent to the dosage received from monochromatic light from a 254 nm low pressure lamp source.

The expression is $$D_{254} = \Sigma_\lambda G(\lambda) D(\lambda) \qquad [1]$$

where $D_{254}$ is the equivalent 254 nm dose, $G(\lambda)$ is the action spectrum of the target microbe, and $D(\lambda)$ is the dose delivered by the polychromatic light source. In this case, the summation will be over the disinfection wavelength region of ~240-290 nm.

Since the irradiance I is the dose divided by the residence time t, $$I_{254} = D_{254}/t \text{ and } I(\lambda) = D(\lambda)/t.$$

Therefore, $$I_{254} t = \Sigma_\lambda G(\lambda) I(\lambda) t \qquad [2]$$

by substituting the values for the dosages into Equation 1. The above expression simplifies to $$I_{254} = \Sigma_\lambda G(\lambda) I(\lambda).$$

For detection of irradiance using a filtered sensor, $$I_{det} = \Sigma_\lambda F(\lambda) S(\lambda) I(\lambda) \qquad [3]$$

where $F(\lambda)$ is the filter response as a function of wavelength, $S(\lambda)$ is the detector response as a function of wavelength and $I(\lambda)$ is the irradiance of the polychromatic light source. If it is intended for the detector to monitor the 254 nm equivalent irradiance, then $$I_{254} = I_{det}.$$

Using Equations 2 and 3 above, $$\Sigma_\lambda G(\lambda) I(\lambda) = \Sigma_\lambda F(\lambda) S(\lambda) I(\lambda).$$

To satisfy this condition, $$G(\lambda) = F(\lambda) S(\lambda). \qquad [4]$$

Equation 4 indicates that the response of a filtered detector should be the same as the action spectrum for the target microbe to detect the equivalent 254 nm irradiance.

The preferred polychromatic sensor element is a radiation sensor device as taught in U.S. provisional patent application Ser. No. 60/506,144 [Knight et al. (Knight)], filed Sep. 29, 2003 and assigned to the assignee of the present invention.

It is possible to use a spectrometer to measure the UV and visible spectra of the fluid (e.g., water) using a cell with a variable path length (e.g., the Ellis system described above). For example, the radiation source could be either a deuterium lamp (light output range ~200-400 nm, 1400 hrs continuous life) or a xenon lamp (light output range ~200-2500 nm, 300-1200 hrs continuous life), depending on the target wavelength range for the spectrum.

Typically, the 200-900 nm wavelength region is available for sampling in fluid such as water. Water absorbs light less than 200 nm, and greater than ~900 nm. Thus, any radiation source or sources that can supply intensity that varies relatively smoothly as a function of wavelength over this region will be adequate. Substantially uniform intensity as a function of wavelength is preferred.

In this embodiment, a particular preferred detector is a spectrophotometer comprising a monochromator with a photodiode array (PDA) or a charged coupled device (CCD) array, that would be capable of obtaining a spectrum without the need to scan through the wavelengths needed. A standard scanning monochromator could also be used, but it is typically bulkier than a monochromator/sensor array system, and a considerable amount of time is necessary to obtain a spectral scan. An example of a compact monochromator/sensor array system is the Ocean Optics S2000 series Miniature Fiber Optic Spectrometer. Another is listed below.

In accordance with this embodiment, spectra at two different path lengths would be compared to eliminate errors due to variations in light intensity, detector responsivity, or window fouling, and can be analyzed to produce polychromatic UVT values. These spectra can also be used to identify specific compounds in the water. This measurement technique has the advantage of providing polychromatic UVT values over any desired wavelength range within the measuring range of the system, and can be weighed in virtually any manner over this wavelength range. It is also possible to utilize a spectroscopic measuring system with a single fixed path length that can scan between 190-720 nm (Isco/Stip brochure "STIP-scan One Sensor for Multiple Parameters", November 2002).

A proposed variable path length spectrometer can be constructed using fiber optics and a light source and spectrometer available from StellarNet Inc (L. Sealey, "Consolidated-Scans-10L30-June 25, 2627-2003-LJS"). The radiation source used in the spectrometer available from StellarNet employs a compact deuterium-halogen lamp. This lamp has good response from 200-850 nm, and is available from the manufacturer with adaptors for fiber optic cable. The spectrometer is also compact with fiber optic cable connections, and has a range of 190-850 nm with simultaneous collection of spectral data using a CCD or photodiode array. Data analysis software for spectral analysis or radiometry is also available and may be readily implemented. A diagram of a proposed variable path length spectrometer that can determine spectra and polychromatic UVT values is shown in FIG. 1. The variable path length cell could be incorporated using the teachings of Ellis, and spectra free of light intensity and fouling variations could be produced.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or alternate embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A process for measuring transmittance of a fluid in a radiation field comprising radiation at a first wavelength and radiation at a second wavelength different from the first wavelength, the process comprising the steps of:
   (i) positioning a polychromatic radiation source and a polychromatic radiation sensor element in a spaced relationship to define a first thickness of fluid in the radiation field;
   (ii) detecting a first radiation intensity corresponding to radiation at the first wavelength received by the sensor element at the first thickness;
   (iii) detecting a second radiation intensity corresponding to radiation at the second wavelength received by the sensor element at the first thickness;
   (iv) altering the first thickness to define a second thickness;
   (v) detecting a third radiation intensity corresponding to radiation at the first wavelength received by the sensor element at the second thickness;
   (vi) detecting a fourth radiation intensity corresponding to radiation at the second wavelength received by the sensor element at the second thickness; and
   (vii) calculating radiation transmittance of the fluid in the radiation field from the first radiation intensity, the second radiation intensity, the third radiation intensity and the fourth radiation intensity.

2. The process defined in claim 1, wherein Steps (ii) and (iii) are conducted substantially concurrently at the first thickness.

3. The process defined in claim 1, wherein Steps (v) and (vi) are conducted substantially concurrently at the second thickness.

4. The process defined in claim 1, wherein Steps (ii) and (iii) are conducted substantially concurrently at the first thickness, and Steps (v) and (vi) are conducted substantially concurrently at the second thickness.

5. The process defined in claim 1, wherein Steps (ii) and (iii) are conducted sequentially at the first thickness.

6. The process defined in claim 1, wherein Steps (v) and (vi) are conducted sequentially at the second thickness.

7. The process defined in claim 1, wherein Steps (ii) and (iii) are conducted sequentially at the first thickness, and Steps (v) and (vi) are conducted sequentially at the second thickness.

8. The process defined in any one of claims 1-7, wherein the polychromatic radiation source comprises an ultraviolet radiation source.

9. The process defined in any one of claims 1-7, wherein the polychromatic radiation source comprises a medium pressure ultraviolet radiation source.

10. The process defined in any one of claims 1-7, wherein the polychromatic radiation source comprises an ultraviolet semiconductor light emitting diode.

11. The process defined in any one of claims 1-7, wherein the sensor element comprises a photodiode.

12. The process defined in any one of claims 1-7, wherein the sensor element comprises a silicon carbide (SiC) photodiode.

13. The process defined in claim 1, wherein the sensor element comprises a filter material interposed between the radiation field and the photodiode.

14. The process defined in claim 1, wherein prior to Step (iv), a radiation intensity is detected at the first thickness for up to each wavelength in the radiation field.

15. The process defined in claim 1, wherein prior to Step (iv), a radiation intensity is detected at the first thickness for each wavelength in the radiation field.

16. The process defined in claim 1, wherein after Step (iv), a radiation intensity is detected at the second thickness for up to each wavelength in the radiation field.

17. The process defined in claim 1, wherein after Step (iv), a radiation intensity is detected at the second thickness for each wavelength in the radiation field.

18. The process defined in claim 1, wherein a radiation intensity is detected at the first thickness for each wavelength in the radiation field.

19. The process defined in claim 1, wherein a radiation intensity is detected at the second thickness for each wavelength in the radiation field.

20. The process defined in claim 1, wherein a radiation intensity is detected at the first thickness and at the second thickness for each wavelength in the radiation field.

21. The process defined in claim 1, wherein the sensor element comprises a spectrometer.

22. The process defined in claim 1, wherein the radiation field comprises radiation in the range of from about 200 nm to about 900 nm.

23. The process defined in claim 1, wherein Step (iv) comprises altering the relative distance between the radiation source and the radiation sensor from a first distance corresponding to the first thickness to a second distance corresponding to the second thickness.

24. The process defined in claim 1, wherein Step (iv) comprises moving the sensor element while keeping the radiation source stationary.

25. The process defined in claim 1, wherein Step (iv) comprises moving the radiation source while keeping the sensor element stationary.

26. The process defined in claim 1, wherein Step (iv) comprises altering the relative linear distance between the radiation source and the radiation sensor.

27. The process defined in claim 1, wherein Step (i) comprises interposing a boundary element between the sensor element and the radiation source to define the first thickness between the boundary element and the radiation source.

28. The process defined in claim 27, wherein Step (iv) comprises altering the relative distance between the boundary element and the radiation source from a first distance corresponding to the first thickness to a second distance corresponding to the second thickness.

29. The process defined in claim 27, wherein Step (iv) comprises moving the boundary element while keeping the radiation source stationary.

30. The process defined in claim 27, wherein Step (iv) comprises moving the radiation source while keeping the boundary element stationary.

31. The process defined in claim 27, wherein Step (iv) comprises altering the relative linear distance between the radiation source and the radiation sensor.

32. The process defined in claim 27, wherein the sensor element is stationary.

33. The process defined in claim 27, wherein Step (iv) comprises altering the first thickness of the radiation field in a step-wise manner.

34. The process defined in claim 27, wherein Step (iv) comprises altering the first thickness of the radiation field in a continuous manner.

* * * * *